United States Patent
Baur et al.

(10) Patent No.: US 8,118,962 B2
(45) Date of Patent: Feb. 21, 2012

(54) METHOD AND APPARATUS FOR SPACING CELLULAR MATTER IN A CELL BLOCK

(75) Inventors: Eric Baur, Marlborough, MA (US); Steven A. Scampini, Groton, MA (US)

(73) Assignee: CYTYC Corporation, Marlborough, MA (US)

( * ) Notice: Subject to any disclaimer, the term of this patent is extended or adjusted under 35 U.S.C. 154(b) by 706 days.

(21) Appl. No.: 12/268,298

(22) Filed: Nov. 10, 2008

(65) Prior Publication Data

US 2009/0165940 A1    Jul. 2, 2009

Related U.S. Application Data

(60) Provisional application No. 61/017,149, filed on Dec. 27, 2007.

(51) Int. Cl.
*G01N 1/30* (2006.01)
*B29C 47/00* (2006.01)

(52) U.S. Cl. ............... 156/245; 435/40.5; 435/40.52; 83/915.5

(58) Field of Classification Search ............. 435/40.51, 435/40.52, 307.1, 40.5; 422/536, 561; 83/915.5
See application file for complete search history.

(56) References Cited

U.S. PATENT DOCUMENTS

| | | | | |
|---|---|---|---|---|
| 2,868,072 A * | 1/1959 | Weiskopf et al. | ............... | 269/7 |
| 2,996,762 A * | 8/1961 | McCormick | ............... | 264/238 |
| 3,014,614 A * | 12/1961 | Carroll et al. | ............... | 220/660 |
| 3,319,289 A * | 5/1967 | McCormick | ............... | 425/117 |
| 3,411,185 A * | 11/1968 | Pickett | ............... | 425/117 |
| 3,456,300 A * | 7/1969 | Pickett | ............... | 425/117 |
| 3,674,396 A * | 7/1972 | McCormick | ............... | 425/117 |
| RE28,165 E * | 9/1974 | McCormick | ............... | 425/117 |
| 3,940,219 A * | 2/1976 | Pickett et al. | ............... | 425/117 |
| 3,982,862 A * | 9/1976 | Pickett et al. | ............... | 425/117 |
| 3,996,326 A * | 12/1976 | Schachet | ............... | 264/158 |
| 4,034,884 A * | 7/1977 | White | ............... | 220/8 |
| 4,220,252 A * | 9/1980 | Beall et al. | ............... | 422/536 |
| 4,276,253 A * | 6/1981 | Adler et al. | ............... | 264/247 |
| 4,569,647 A * | 2/1986 | McCormick | ............... | 425/117 |
| 4,623,308 A * | 11/1986 | Hellon | ............... | 425/117 |
| 4,801,553 A * | 1/1989 | Owen et al. | ............... | 436/174 |
| 4,914,022 A * | 4/1990 | Furmanski et al. | ............... | 435/7.21 |

(Continued)

FOREIGN PATENT DOCUMENTS
JP         60076643 A  *  5/1985

*Primary Examiner* — Philip Tucker
*Assistant Examiner* — William Bell
(74) *Attorney, Agent, or Firm* — Vista IP Law Group LLP

(57) ABSTRACT

Methods and apparatus for bonding block of paraffin having cellular material embedded at one end thereof with an additional amount of paraffin are disclosed, including a method comprising placing the paraffin block in a well of a mold with the paraffin-embedded cellular material positioned on a support structure that elevates the cellular matter from a bottom surface of the well; heating the mold to thereby soften and at least partially melt and blend together the embedding paraffin and additional paraffin located in the well, the support structure sized such that some of the additional paraffin flows on the bottom surface of the well at least partially surrounding the support structure; and cooling the mold to thereby bond the additional paraffin to the embedding paraffin and re-solidify the paraffin block, wherein the retained cellular matter is spaced apart from an end of the re-solidified paraffin block defined by the bottom surface of the well.

9 Claims, 5 Drawing Sheets

U.S. PATENT DOCUMENTS

| | | | | |
|---|---|---|---|---|
| 5,080,869 A * | 1/1992 | McCormick | | 422/547 |
| 5,424,040 A * | 6/1995 | Bjornsson | | 422/536 |
| 5,427,742 A * | 6/1995 | Holland | | 422/536 |
| 5,665,398 A * | 9/1997 | McCormick | | 425/117 |
| 5,817,032 A * | 10/1998 | Williamson et al. | | 600/562 |
| 6,017,476 A * | 1/2000 | Renshaw | | 264/158 |
| 6,387,653 B1 | 5/2002 | Voneiff et al. | | 435/40.52 |
| 6,913,921 B2 * | 7/2005 | Fischer | | 435/308.1 |
| 7,005,110 B2 * | 2/2006 | Taft et al. | | 422/536 |
| 7,156,814 B1 * | 1/2007 | Williamson et al. | | 600/562 |
| 7,179,424 B2 * | 2/2007 | Williamson et al. | | 422/536 |
| 7,521,021 B2 * | 4/2009 | McCormick | | 422/536 |
| 7,541,161 B2 * | 6/2009 | Fischer | | 435/40.5 |
| 7,776,274 B2 * | 8/2010 | Williamson et al. | | 422/400 |
| 7,780,919 B2 * | 8/2010 | McCormick | | 422/536 |
| 7,829,021 B2 * | 11/2010 | Hutchins et al. | | 422/63 |
| 7,914,738 B2 * | 3/2011 | Hutchins et al. | | 422/63 |
| 7,927,564 B2 * | 4/2011 | McCormick | | 422/561 |
| 7,975,586 B2 * | 7/2011 | McCormick | | 83/651 |
| 2004/0121456 A1 * | 6/2004 | Fischer | | 435/297.2 |
| 2005/0084425 A1 * | 4/2005 | Williamson et al. | | 422/102 |
| 2005/0112034 A1 * | 5/2005 | McCormick | | 422/102 |
| 2005/0147538 A1 * | 7/2005 | Williamson et al. | | 422/102 |
| 2007/0104618 A1 * | 5/2007 | Williamson et al. | | 422/102 |
| 2007/0116612 A1 * | 5/2007 | Williamson, IV | | 422/102 |
| 2007/0140920 A1 * | 6/2007 | McCormick | | 422/102 |
| 2007/0166834 A1 * | 7/2007 | Williamson et al. | | 436/174 |
| 2008/0057573 A1 * | 3/2008 | Hutchins et al. | | 435/307.1 |
| 2008/0081351 A1 * | 4/2008 | Hutchins et al. | | 435/30 |
| 2008/0081363 A1 * | 4/2008 | Hutchins et al. | | 435/286.4 |
| 2008/0138854 A1 * | 6/2008 | Williamson | | 435/40.52 |
| 2008/0280351 A1 * | 11/2008 | Fischer | | 435/287.1 |
| 2009/0098640 A1 * | 4/2009 | Fischer | | 435/283.1 |
| 2009/0246825 A1 * | 10/2009 | McCormick | | 435/40.52 |
| 2009/0253199 A1 * | 10/2009 | McCormick | | 435/309.1 |
| 2009/0256279 A1 * | 10/2009 | Lee et al. | | 264/225 |
| 2010/0184127 A1 * | 7/2010 | Williamson et al. | | 435/40.52 |
| 2010/0278627 A1 * | 11/2010 | Williamson et al. | | 414/800 |
| 2010/0330660 A1 * | 12/2010 | Hutchins et al. | | 435/286.4 |

* cited by examiner

METHOD AND APPARATUS FOR SPACING CELLULAR MATTER IN A CELL BLOCK

RELATED APPLICATION DATA

The present application claims the benefit under 35 U.S.C. §119 to U.S. provisional patent application Ser. No. 61/017, 149, filed Dec. 27, 2007. The foregoing application is hereby incorporated by reference into the present application in its entirety.

FIELD OF THE INVENTION

The present invention pertains to methods and apparatus for preparing cells for microscopic examination, and more particularly to automated and semi-automated systems and methods for embedding cellular materials and tissue fragments within a paraffin substrate that may be thereafter thinly-cut using a standard microtome, for microscope examination.

BACKGROUND

It is useful for diagnosing or detecting a disease process to perform a histologic or cytologic examination of a tissue cell sample using a light microscope. This requires that a tissue (cellular material) sample must first be retrieved from the patient, and then processed for microscopic examination. A number of minimally invasive techniques are available for retrieving and collecting cell samples from a patient, e.g., by using a fine needle aspiration biopsy, or by brushing body cavity surfaces accessible through minimally invasive endoscopic techniques. A variety of cell sample processing techniques are also known, such as the Cytospin® technique and the Thin-prep® technique, for depositing cellular materials and tissue fragments directly onto a microscope slide. Another technique, commonly referred to as a cell block preparation, immobilizes cellular materials and/or small tissue fragments within a solid support structure, typically paraffin. Thin sections of the cell block are then cut with a microtome and mounted onto a microscope slide for examination.

U.S. Pat. No. 6,913,921 ("the '921 patent") discloses and describes methods and apparatus for cell block preparation, including providing a tissue collection cassette that serves a dual function of capturing cellular sample matter and providing a fluid pathway through which the cell processing and embedding reagents can flow. The cellular sample material is provided in an aqueous solution or a liquid cell preservative, which is passed through the tissue cassette across a filter that traps the cells and tissue fragments. A reagent flow pathway is configured to sequentially pass embedding reagents (alcohol, xylene, eosin stain) and liquefied paraffin through the tissue cassette and the cell sample already deposited on the filter. Once the paraffin is cooled, the filter is peeled away, leaving a paraffin "disk" protruding from the tissue cassette, with embedded cellular matter positioned at the end of the disk in a plane at which a tissue section can be cut using a standard microtome for microscope examination.

U.S. patent application Ser. No. 11/839,533, filed Aug. 15, 2007, and assigned to the assignee of the present invention ("the '533 application"), discloses a substantially automated cell block creation that does not require human oversight, including a two-piece cassette and filter assembly, to achieve more consistent cellular matter quantities in the created cell blocks, shorter processing time, reduced use of hazardous reagents, and more fully encapsulated cell blocks to preserve nucleic acid integrity. The contents of the '921 patent and '533 application are hereby fully incorporated by reference.

Upon completion of a cell block using the disclosed processes of the '921 patent and '533 application, a "re-melting" step is employed in order to transform the cell face shape from circular to square and more fully encapsulate the "cell spot" (the layer of cells collected cells from the cell block formation process), so that it may be processed on a standard microtome. In doing so, however, the (still circular) cell spot remains positioned at the "bottom" of the embedding mold, and outer surface of the cell block. However, many histologists would prefer to have an additional layer (volume) of wax between the end of the protruding wax block and the cell spot.

SUMMARY OF THE DISCLOSED INVENTIONS

Embodiments of the present invention are directed to providing an additional layer (volume) of paraffin, or other sectionable substance between the cell spot of collected cellular matter and a distal end of a protruding paraffin-embedded cell block created using an automated (or semi-automated) process. The additional layer of wax spaces the cell spot away from the end surface of the cell block, while it remains in a plane parallel to the end surface, such that, when the cell block is cut on a microtome, the operator is first cutting cell-free wax sections, allowing adjustments to be made to the microtome before encountering the cell layer.

In one embodiment, a method is provided for bonding block of paraffin having cellular material embedded at one end thereof with an additional amount of paraffin, the method including: placing the paraffin block in a (preferably rectangular) well of a mold with the paraffin-embedded cellular material positioned on a support structure that elevates the cellular matter from a bottom surface of the well; heating the mold to thereby soften and at least partially melt and blend together the embedding paraffin and additional paraffin located in the well, the support structure sized such that some of the additional paraffin flows on the bottom surface of the well at least partially surrounding the support structure; and cooling the mold to thereby bond the additional paraffin to the embedding paraffin and re-solidify the paraffin block, wherein the retained cellular matter is spaced apart from an end of the re-solidified paraffin block defined by the bottom surface of the well. Heating and cooling of the mold may be controlled using a heating and cooling mechanism placed in thermal contact with the mold. The support structure may comprise a raised, integral portion of the bottom surface of the well, or alternatively a spacer placed loosely on, or adhered to, the bottom surface of the well. By way of non-limiting example, the spacer may be a sectionable filter membrane, such as one made of nitrocellulose.

In another embodiment, a method is provided for forming a cell block, the method including: dispensing a sample fluid across a filter until a desired amount of cellular material carried in the sample fluid is retained by the filter; dispensing liquefied paraffin over the filter and allowing the paraffin to solidify to thereby form a substantially solid block of paraffin with the retained cellular material embedded at one end of the paraffin block against the filter; removing filter from the paraffin block; placing the paraffin block in a well of a mold with the paraffin-embedded cellular material positioned on a support structure that elevates the cellular matter from a bottom surface of the well; heating the mold to thereby soften and at least partially melt and blend together the embedding paraffin and additional paraffin located in the well, the support structure sized such that some of the additional paraffin flows on the bottom surface of the well at least partially surrounding the support structure; and cooling the mold to thereby bond the additional paraffin to the embedding paraffin and re-solidify the paraffin block, wherein the retained cellular matter is spaced apart from an end of the re-solidified paraffin block defined by the bottom surface of the well. Again, heating and cooling of the mold is controlled using a heating and cooling mechanism placed in thermal contact with the mold, and the support structure may comprise a raised, integral portion of the bottom surface of the well, or a spacer placed loosely on, or adhered to, the bottom surface of the well. For example, the spacer may be a sectionable filter membrane placed loosely on the bottom surface of the well.

In yet another embodiment, an apparatus for bonding a block of paraffin having cellular material embedded at one end thereof with an additional amount of paraffin is provided, the apparatus comprising a thermally conductive re-melt tray having a well formed therein, the well having substantially rectangular dimensions including side walls and a bottom surface, and a support platform positioned in a center area of the well, the support platform raised from the bottom surface and sized to accommodate placement thereon of the respective end of the paraffin block with the embedded cellular matter, while allowing for the additional paraffin to substantially fill a volume at least partially surrounding the paraffin block and defined by the bottom surface and the side walls of the well. The heating and cooling mechanism preferably has a thermally conductive surface configured for controllably heating and cooling the re-melt tray. The support structure may be a raised, integral portion of the bottom surface of the well. Alternatively, the support structure may be a spacer placed loosely on (e.g., a sectionable filter membrane), or adhered to, the bottom surface of the well.

In still another embodiment, a method for forming a cell block includes dispensing a sample fluid across a sectionable filter membrane until a desired amount of cellular material carried in the sample fluid is retained by the filter membrane, and dispensing liquefied paraffin over the filter and allowing the paraffin to solidify to thereby form a substantially solid block of paraffin with the retained cellular material embedded at one end of the paraffin block against the sectionable filter membrane.

Other and further aspects and embodiments of the disclosed inventions are described in the detailed description of the accompanying drawings.

BRIEF DESCRIPTION OF THE DRAWINGS

It will be appreciated that the system and apparatus shown in the drawings are not necessarily drawn to scale, with emphasis instead being placed on illustrating the various aspects and features of the illustrated embodiments, in which.

DETAILED DESCRIPTION OF THE ILLUSTRATED EMBODIMENTS

Cell Block Process Without Using Embodiments of the Invention

Figure 1:
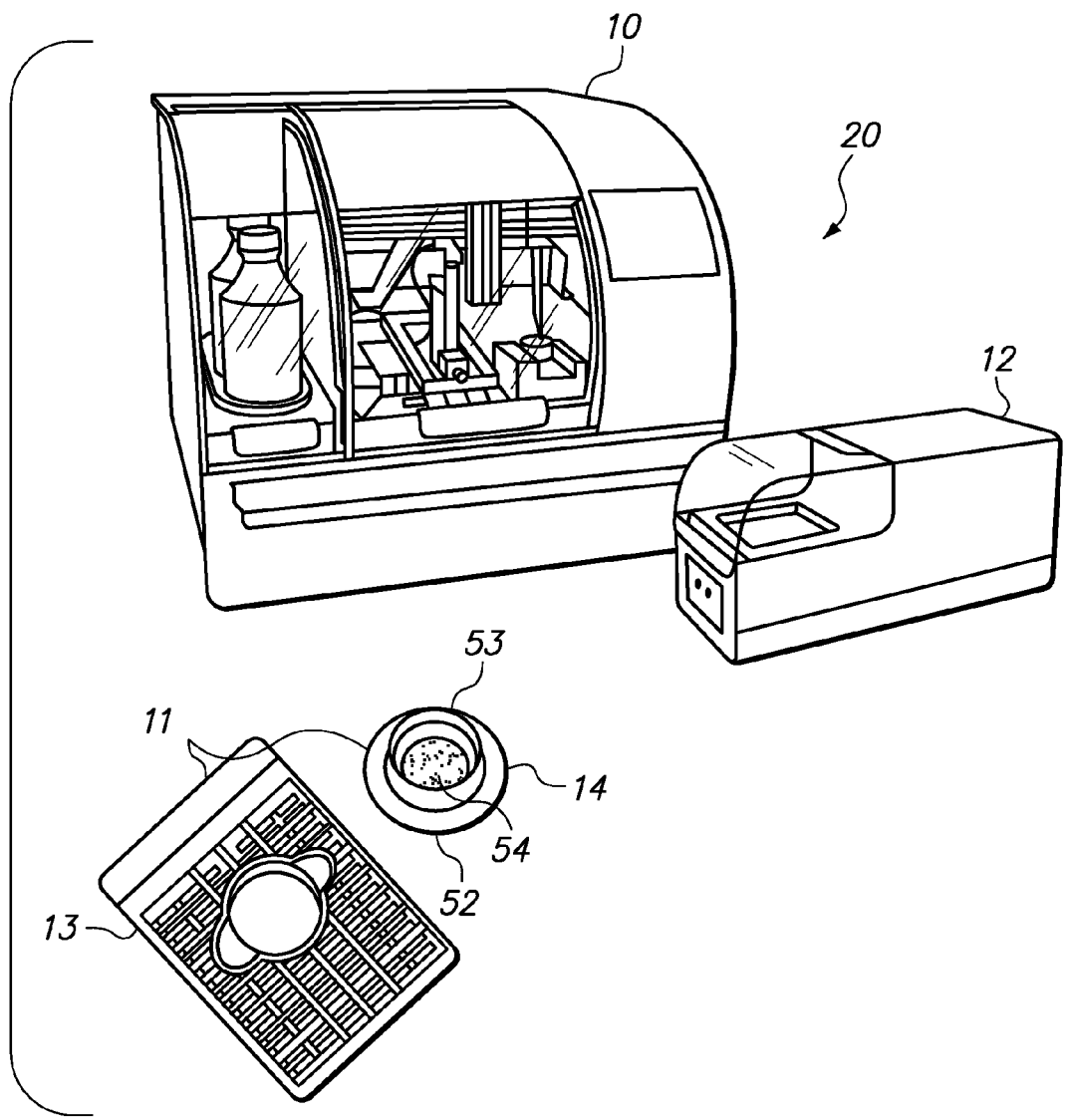
FIG. 1 is a perspective view an exemplary cell block preparation system including a processing station, a cell block cassette with detachable filter, and a finishing station.

FIG. 1. depicts the main components of an exemplary cell block processing system 20, including a cell block processing station 10, a two-piece cell block cassette 11 (including a main cassette body 13 and a detachable filter assembly 14) which captures the captures the cellular material and guides infusion of the reagents and paraffin, and a finishing station 12 for encapsulating a newly created cell block in additional paraffin in preparation for later cutting and slide preparation.

Figure 2:
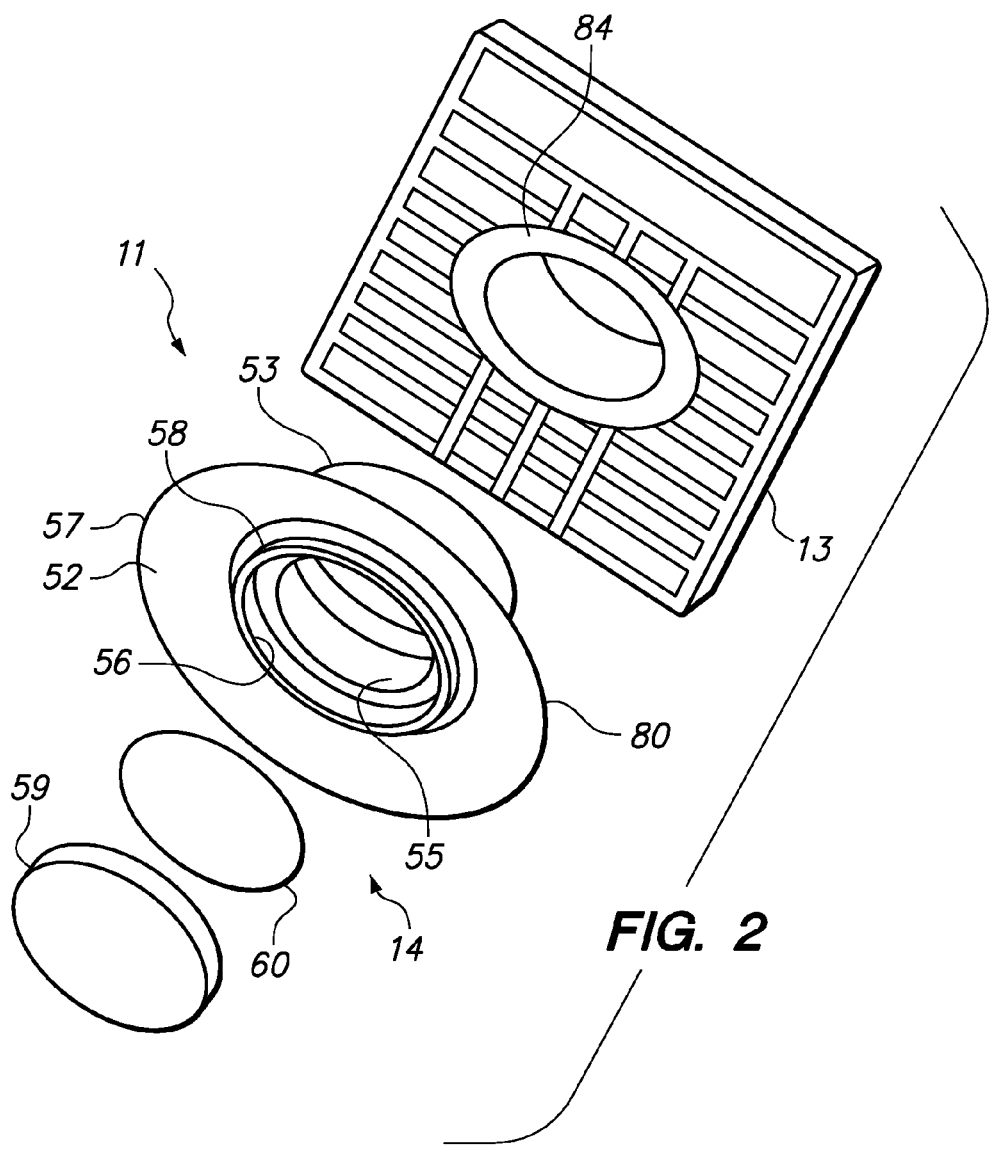
FIG. 2 is an exploded perspective view of the cell block cassette and filter assembly used in the system of FIG. 1.

Referring also to FIG. 2, the filter assembly 14 comprises a single-piece housing or body 80 having a base portion 52 forming the sealing surface, and a neck portion 53 extending from the base portion 52. The neck portion 53 defines a perimeter 55 of the collection well 54, and has a top end that makes an interference fit with an annular grove 84 located in a bottom surface of the main cassette body 13 in order to detachably attach the filter assembly 14 to the main cassette body 13. The filter assembly housing further comprises a filter support retention portion 56 extending from an underside of the base portion 52, with a thermally conductive porous filter support member, e.g., a sintered metal disc or other thermally conductive porous support 59 (such as a metal screen or solid thermally conductive disc with holes punched in it) retained therein, the filter 60 being positioned atop the filter support member 59 within the collection well 54. The base portion sealing surface slopes at a downward angle from the neck portion, such that an outermost edge 57 of the sealing surface extends to (or beyond) an outermost edge 58 of the filter support retention portion 56 in order to form a seal with a waste chamber interface (not shown) in the processing station 10.

In particular, cells must be contained on the filter 60, while sample fluid, stain, reagents and paraffin are allowed to pass through and be discarded in the waste chamber, leaving only cells and hardened paraffin wax behind. The filter may be heat staked across a bottom area of the (polyester) housing 80 to define turn the collection well 54. The housing (or filter holder) 80 and attached (heat staked) filter 60 define the collection well 54 for the various liquids and wax to form a hardened protrusion from the mating cassette body 13. This filter allows the fluids to pass through but leave cells to collect on the surface of the membrane. As described in the '533 application, a vacuum is employed in the process to pull fluid through the filter, so a metal or other hard support member 59 is used to keep the filter 60 from being pulled into the waste chamber by the vacuum. The filter support member 59 (in one embodiment, a sintered bronze or other metal disc) provides a porous, thermally conductive support to be pressed against the filter membrane 60, and has a porosity, such as 80 microns, to allow fluid to easily continue to pass through the filter assembly after passing through the much smaller filter pores.

Figure 3:
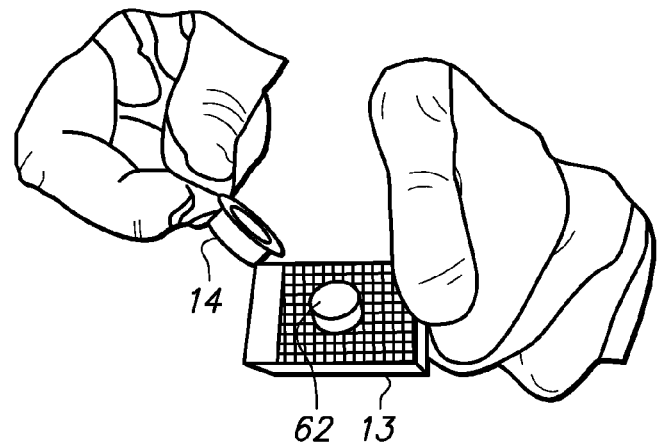
FIG. 3 depicts a user detaching the filter assembly from the cell block cassette following creation of a new cell block using the system of FIG. 1.

The sealing surface of the base portion 52 forms a vacuum seal on the outer sealing edge of the waster chamber interface (not shown) when the cassette is seated (and latched into) the cassette interface in the processing station 10. The compliant nature of the outer plastic "mushroom" shape of the sealing surface 52 provides both adequate vacuum sealing and a proper preload when compressed to withstand the pressure applied to the under surface during back pulsing (pressurized air pulsing). The sealing surface of the base 52 also provides the system operator with a graspable means to remove the filter assembly 14 from the main cassette body 13, thus leaving behind a solid protrusion of paraffin wax containing a layer of cells at the very top end of the wax protrusion when the cell block has been processed. For purposes of illustration, FIG. 3 depicts an operator detaching the filter assembly 14 from the cell block cassette 13 following creation of a new cell block 62. In order to separate the filter assembly 14 from the main cassette body 13, it may be advisable to first chill the already solidified paraffin to cause further thermal contraction of same. This can be accomplished, for example, by spraying a cold gas (compressed air) onto the cell block or placing it in a freezer for a short period of time. As the wax contracts, it releases from the respective filter and support member.

Figure 4:
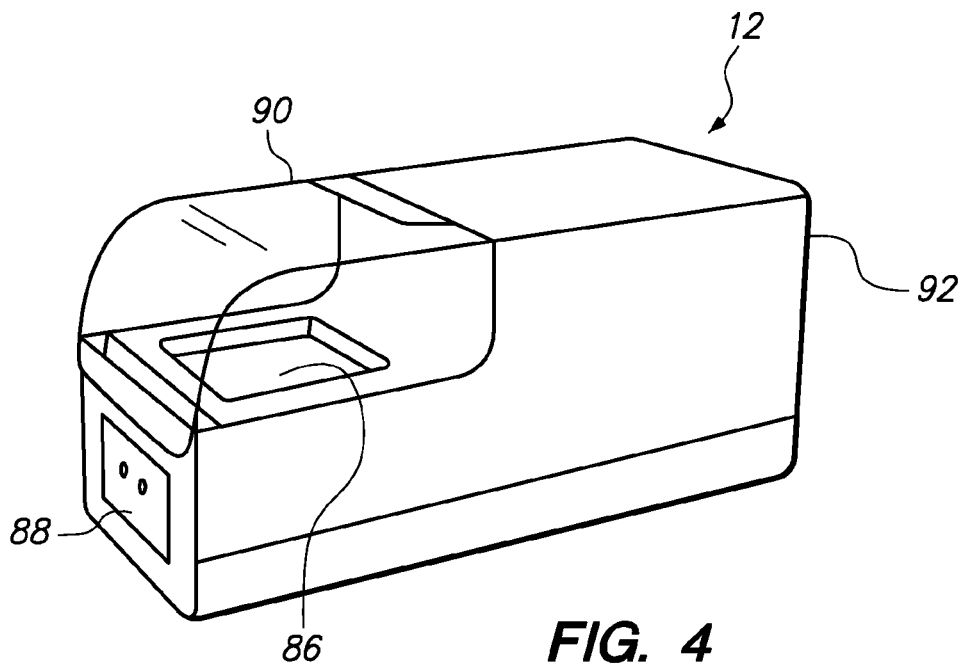
FIG. 4 is a perspective view of the finishing station of the system of FIG. 1.
Figure 5A:
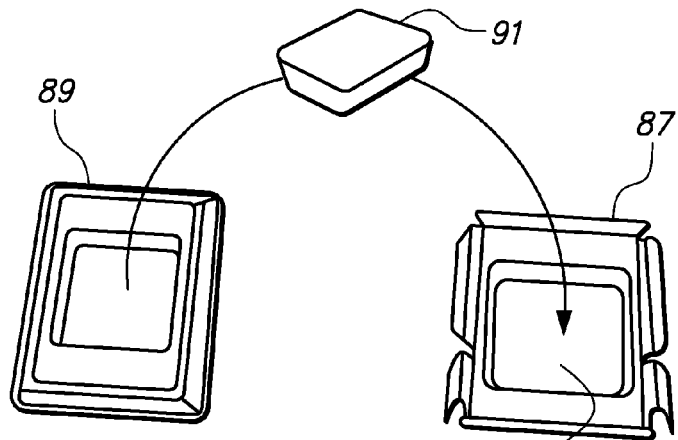
FIGS. 5A-5C depict placement of an additional paraffin block and cell block cassette together in a thermally conductive mold used for bonding the previously formed paraffin cell block with an additional amount of paraffin using the finishing station.
Figure 5B:
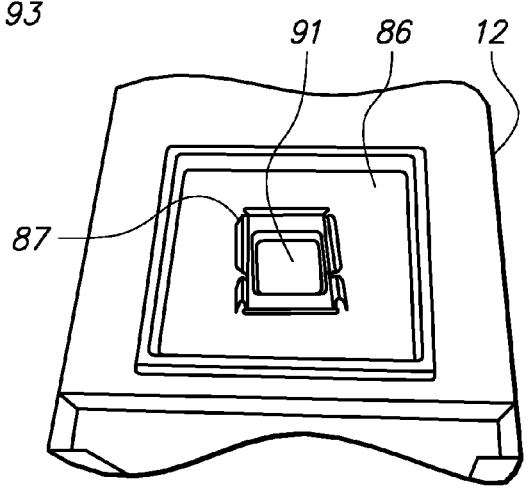
Figure 5C:
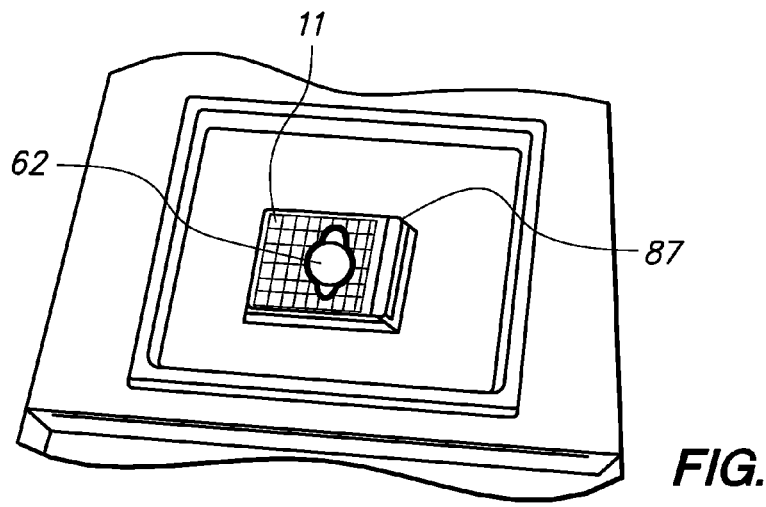

FIG. 4 is a perspective view of the finishing station 12, which generally includes a housing 92 for enclosing the processor and electronics and heat exchanger, a thermally conductive heating/cooling plate 86, a simple user-interface (control panel) 88 (FIG. 6), and a clear plastic cover 90 for the heating/cooling plate 86. As illustrated in FIGS. 5A-5C, the finishing station 12 is used to embed the cell block in additional paraffin, in particular the end of the cell block containing the cell layer. In particular, a piece of paraffin 91 is first transferred from its packaging 89 into the re-melt well 93 of thermally conductive (e.g., stamped metal) embedding mold 87 (FIG. 5A). The embedding mold 87 is then on the heating/cooling plate 86 on the finishing station 12 (FIG. 5B), and the operator starts the unit using the user interface 88 begin melting the wax 91. When the embedding wax 91 is completely melted (about seven minutes), the cell block cassette 11 is placed into the well 93 of the mold 87 by fitting one end into the mold 87 and lowering the cassette until it is fully inserted into the mold, with the cell block paraffin side face side and into the liquid paraffin.

Preferably, no air bubbles are trapped between the melted paraffin and the cell block paraffin. The unit then continues to apply heat to the plate 86, until the embedding paraffin on the cell block has softened and started to melt. At this point, the plate is abruptly switched over to cooling. In particular, it is important that the re-melt process employ be fast and controlled heating, followed by fast and controlled cooling. In one embodiment, a method for the paraffin re-melt includes placing the paraffin-embedded cellular material atop an additional amount of paraffin; controllably heating to thereby soften and at least partially blend together the embedding paraffin and additional paraffin, without softening or liquefying the embedding paraffin to a point that the retained cellular material therein breaks apart and disburses through the embedding paraffin; and controllably cooling to thereby bond the additional paraffin to the embedding paraffin.

Cell Block Process Using Embodiments of the Invention

In accordance with embodiments of the invention, methods and apparatus are provided for bonding a cell block, i.e., a block of paraffin having cellular material embedded at one end thereof, with an additional amount of paraffin in order to both shape the block in rectangular form for sectioning on a standard microtome, and for adding an extra layer of paraffin or another substance between the very end of the cell block and the cellular material.

Figure 7:
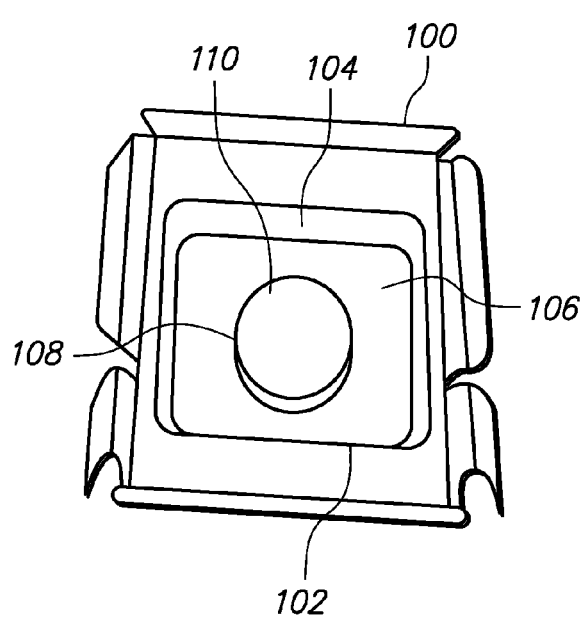
FIG. 7 is an alternate thermally conductive mold used for bonding a previously formed paraffin cell block with an additional amount of paraffin, according to one embodiment of the invention.

FIG. 7 depicts one embodiment of the invention, comprising a thermally conductive re-melt tray 100 having a well 102 formed therein, the well 102 having substantially rectangular dimensions, including side walls 104 and a bottom surface 106, with a raised support platform 108 positioned in a center area of the well 102. In particular, the support platform 108 is elevated from the bottom surface 106 and sized to accommodate placement thereon of the respective end (or "face") of a paraffin cell block containing the embedded cellular matter and attached to a cell block cassette, while allowing for additional paraffin (not shown) placed in the well 102 to substantially fill a volume at least partially surrounding the platform 108 and, thus, the paraffin cell block, the volume being defined by the respective bottom surface 106 and the side walls 104 of the well 102.

Thus, the foregoing described embodiment also provides a method A method for bonding block of paraffin having cellular material embedded at one end thereof with an additional amount of paraffin, the method including placing the paraffin block in a well of a mold with the paraffin-embedded cellular material positioned on a support structure that elevates the cellular matter from a bottom surface of the well, heating the mold to thereby soften and at least partially melt and blend together the embedding paraffin and additional paraffin located in the well, the support structure sized such that some of the additional paraffin flows on the bottom surface of the well at least partially surrounding the support structure, and cooling the mold to thereby bond the additional paraffin to the embedding paraffin and re-solidify the paraffin block, wherein the retained cellular matter is spaced apart from an end of the re-solidified paraffin block defined by the bottom surface of the well.

More specifically, the foregoing embodiment may be used in conjunction with the previously described embodiments of the '533 application to provide a method for forming a cell block, including dispensing a sample fluid across a filter until a desired amount of cellular material carried in the sample fluid is retained by the filter, dispensing liquefied paraffin over the filter and allowing the paraffin to solidify to thereby form a substantially solid block of paraffin with the retained cellular material embedded at one end of the paraffin block against the filter, removing filter from the paraffin block, placing the paraffin block in a well of a mold with the paraffin-embedded cellular material positioned on a support structure that elevates the cellular matter from a bottom surface of the well, heating the mold to thereby soften and at least partially melt and blend together the embedding paraffin and additional paraffin located in the well, the support structure sized such that some of the additional paraffin flows on the bottom surface of the well at least partially surrounding the support structure, and cooling the mold to thereby bond the additional paraffin to the embedding paraffin and re-solidify the paraffin block, wherein the retained cellular matter is spaced apart from an end of the re-solidified paraffin block defined by the bottom surface of the well.

Figure 6:
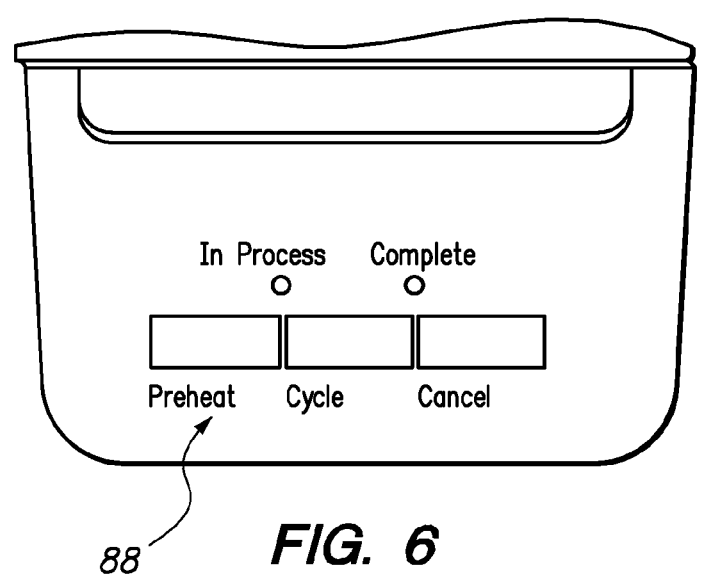
FIG. 6 shows the user interface on the finishing station.
Figure 8A:
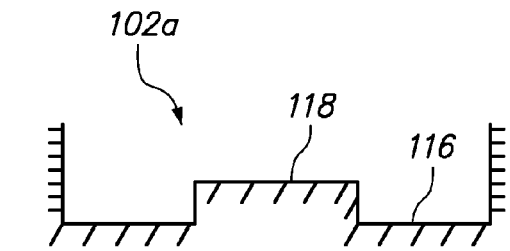
FIGS. 8A-8C are cut-away side views of variations of the thermally conductive mold of FIG. 7, according to further embodiments of the invention.
Figure 8B:
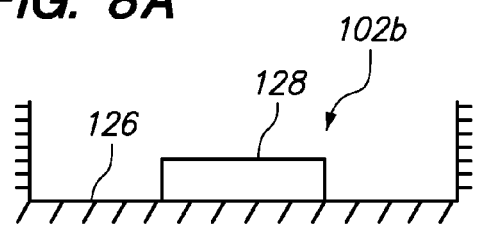

As with the embodiments depicted in FIGS. 4-6, the re-melt tray 100 is configured for use with a heating and cooling mechanism, such as the finishing station 12, having a thermally conductive surface configured for controllably heating and cooling the re-melt tray 100. In various embodiments of the invention, the support structure 108 may be a raised, integral portion of the bottom surface 106 of the well 102, such as support structure 118 shown in FIG. 8A, which is a raised, integral portion of a bottom surface 116 of re-melt well 102a. Alternatively, the support structure 108 may be a spacer placed loosely on the bottom surface 106 of the well 102, such as support structure 128 shown in FIG. 8B, which is resting on (but unattached to) a bottom surface 126 of re-melt well 102b. Further alternatively, the support structure 108 may be a spacer adhered (e.g., glued) to the bottom surface 106 of the well 102, such as support structure 138 shown in FIG. 8C, which is attached by a layer of adhesive 135 to a bottom surface 136 of re-melt well 102c.

Figure 8C:
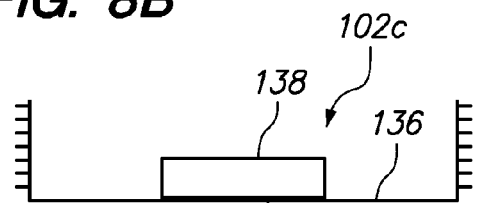

The re-melt trays (or "embedding mold") of the foregoing embodiments may be made of a thermally conductive sheet metal or copper machined part that is rectangular in shape to match the cell block cassette, e.g., the two-piece cassette 11 shown in FIGS. 1-2. Thus, upon completion of the re-melting step there will be a rectangular "window of wax" with a circular center missing (where the raised platform 108, 118, 128, 138) was located, to thereby provide a thickness of wax for histologists to initially cut through when processing the cell block on a microtome. The spacer may also be made of a thermally conductive metal, such as copper, or alternatively, of a plastic having a relatively high melting temperature. Use of an adhesive (such as depicted in FIG. 8C) to attach the spacer to the bottom surface of the well can avoid centering problems that may otherwise occur due to movement of the spacer relative to the bottom well surface during the re-melt (or "embedding") process. Of course, the adhesive and plastic material will need to withstand the temperatures experienced during the embedding process.

Figure 9:
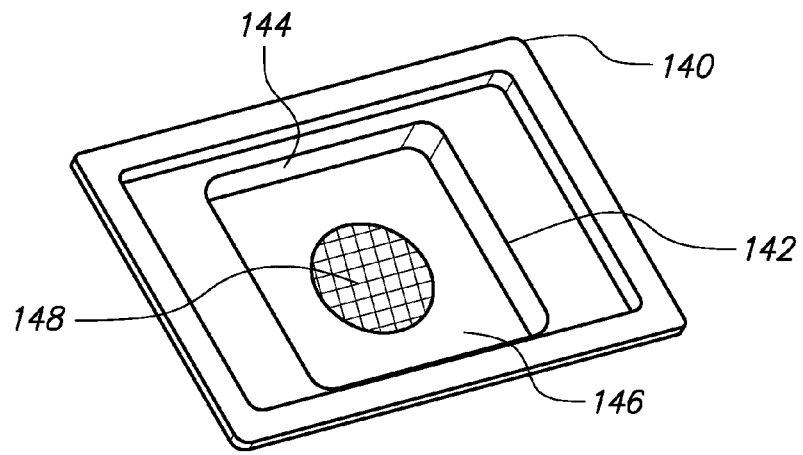
FIG. 9 is a further alternate thermally conductive mold used for bonding a previously formed paraffin cell block with an additional amount of paraffin, according to still another embodiment of the invention.

FIG. 9 depicts another embodiment of a thermally conductive re-melt tray 140 having a well 142 formed therein, the well 142 having substantially rectangular dimensions, including side walls 144 and a bottom surface 146. A spacer comprising a nitrocellulose or other sectionable filter membrane 148 that is sectionable (by the microtome), is positioned (unattached) in a center area on the bottom surface 146 of the well 142 to mimic the same effect as the raised platform 108 in FIG. 7. In particular, the filter membrane 148 is elevated from the bottom surface 146 of the well 142, and sized to accommodate placement thereon of the cell block face containing the embedded cellular matter and attached to a cell block cassette, while allowing for additional paraffin (not shown) placed in the well 102 to substantially fill a volume at least partially surrounding the filter 148 and, thus, the paraffin cell block, the volume being defined by the respective bottom surface 146 and the side walls 144 of the well 142. The sectionable filter member 148 becomes embedded in the re-melted and re-solidified cell block, requiring histologists to first cut through the filter membrane 148 before arriving at the cellular matter (or cell spot) on the microtome.

Alternatively, in accordance with a further embodiment of the invention, the use of a sectionable filter in the assembly placed at the proper location in the path of fluid flow during creation of the cell block would allow for a desired spacing of the cells away from the end (face) of the completed cell block. Towards this end, the original filter used on the filter holder and cassette assembly may be made of a sectionable material and not removed from the originally formed cell block. In accordance with this aspect, a method for forming a cell block includes dispensing a sample fluid across a sectionable filter membrane until a desired amount of cellular material carried in the sample fluid is retained by the filter membrane, and dispensing liquefied paraffin over the filter and allowing the paraffin to solidify to thereby form a substantially solid block of paraffin with the retained cellular material embedded at one end of the paraffin block against the sectionable filter membrane.

In yet another alternate embodiment of the invention, waxes having different melting temperatures are used in successive re-melt phases to deposit the extra layer of wax to the face of the cell block. In particular, a first re-melt phase is conducted as described above in conjunction with FIGS. 4-6 to give the face of the cell block a rectangular dimension for compatibility with the microtome. Then, a second "re-melt" process is undertaken to bond a further, thin layer of wax to the cell block face to space the cell spot away from the end surface. The added wax layer has a slightly lower melting temperature than the cell block wax so that it can be well-bonded to the face of the cell block, without melting the wax of the cell block to a degree which allows the cells to drift apart and/or sink down into the newly added layer at the end of the face, thereby compromising the planarity and positioning of the cell layer.

In accordance with this further embodiment, a method is provided for bonding a cell block of paraffin having cellular material embedded at one end thereof with additional amounts of paraffin, the method including placing the cell block along with a first quantity of additional paraffin in a well of a mold, the well being substantially rectangular in dimension, the first quantity of additional paraffin having a melting temperature substantially the same as a melting temperature of the cell block paraffin; heating the mold to soften and at least partially melt and blend together the cell block paraffin and first quantity of additional paraffin, wherein the combined paraffin assumes the dimensions of the well; cooling the mold to re-solidify the cell block; placing the re-solidified cell block in the same or a different mold along with a second quantity of additional paraffin, the second quantity of additional paraffin having a melting temperature lower than the melting temperature of the re-solidified cell block paraffin; heating said same or different mold to melt the second additional quantity of paraffin, and at least soften the re-solidified cell block paraffin, to allow for bonding of the two; and cooling said same or different mold to again re-solidify the cell block, wherein the retained cellular matter is spaced apart from an end of the again re-solidified cell block by a layer of the second additional quantity of paraffin.

The invention may be embodied in other specific forms besides and beyond those described herein. The foregoing embodiments are therefore to be considered in all respects illustrative rather than limiting.

What is claimed is:

1. A method for bonding a cell block of paraffin having cellular material embedded at one end thereof with an additional amount of paraffin, comprising:

placing the paraffin block in a well of a mold with the paraffin-embedded cellular material positioned on a support structure that elevates the cellular matter from a bottom surface of the well;

heating the mold to thereby soften and at least partially melt and blend together the cell block paraffin and additional paraffin located in the well, the support structure sized such that some of the additional paraffin flows on the bottom surface of the well at least partially surrounding the support structure; and cooling the mold to thereby bond the additional paraffin to the embedding paraffin and re-solidify the paraffin block, wherein the retained cellular matter is spaced apart from an end of the re-solidified paraffin block defined by the bottom surface of the well.

2. The method of claim 1, wherein heating and cooling of the mold is controlled using a heating and cooling mechanism placed in thermal contact with the mold.

3. The method of claim 1, wherein the support structure comprises a raised, integral portion of the bottom surface of the well.

4. The method of claim 1, wherein the support structure comprises a spacer placed on the bottom surface of the well.

5. The method of claim 4, wherein the spacer is a sectionable filter membrane.

6. The method of claim 5, wherein the sectionable filter membrane comprises nitrocellulose.

7. The method of claim 4, wherein the spacer is adhered to the bottom surface of the well.

8. The method of claim 1, wherein the well has rectangular dimensions.

9. A method for bonding a cell block of paraffin having cellular material embedded at one end thereof with additional amounts of paraffin, comprising:

placing the cell block along with a first quantity of additional paraffin in a well of a mold, the well being substantially rectangular in dimension, the first quantity of additional paraffin having a melting temperature substantially the same as a melting temperature of the cell block paraffin;

heating the mold to soften and at least partially melt and blend together the cell block paraffin and first quantity of additional paraffin, wherein the combined paraffin assumes the dimensions of the well;

cooling the mold to re-solidify the cell block;

placing the re-solidified cell block in the same or a different mold along with a second quantity of additional paraffin, the second quantity of additional paraffin having a melting temperature lower than the melting temperature of the re-solidified cell block paraffin;

heating said same or different mold to melt the second additional quantity of paraffin, and at least soften the re-solidified cell block paraffin, to allow for bonding of the two; and cooling said same or different mold to again re-solidify the cell block, wherein the retained cellular matter is spaced apart from an end of the again re-solidified cell block by a layer of the second additional quantity of paraffin.

* * * * *